United States Patent [19]
N'Guyen

[11] Patent Number: 5,917,189
[45] Date of Patent: Jun. 29, 1999

[54] COLLIMATOR WITH MULTIPLE FIELD OF VIEW AND A MEDICAL IMAGING SYSTEM INCLUDING A COLLIMATOR OF THIS TYPE

[75] Inventor: Trung N'Guyen, Le plessis Robinson, France

[73] Assignee: SMV International, Buc Cedex, France

[21] Appl. No.: 08/867,367

[22] Filed: Jun. 2, 1997

[30] Foreign Application Priority Data

Jun. 6, 1996 [FR] France ..................................... 96 06990

[51] Int. Cl.$^6$ ..................................... G01T 1/164
[52] U.S. Cl. ............................................... 250/363.1
[58] Field of Search .......................................... 250/363.1

[56] References Cited

U.S. PATENT DOCUMENTS

| | | |
|---|---|---|
| 4,136,283 | 1/1979 | Blum . |
| 4,250,392 | 2/1981 | Leask et al. . |

FOREIGN PATENT DOCUMENTS

| | | | |
|---|---|---|---|
| 0 698 894 A1 | 2/1996 | European Pat. Off. . | |
| 2640054 | 6/1990 | France . | |
| 54-102184 | 8/1979 | Japan | ................................. 250/363.1 |
| 58-018180 | 2/1983 | Japan . | |
| 58-223081 | 12/1983 | Japan | ................................. 250/363.1 |
| 7-307288 | 11/1995 | Japan . | |

*Primary Examiner*—Constantine Hannaher
*Attorney, Agent, or Firm*—Nilles & Nilles SC

[57] ABSTRACT

A collimator intended to be mounted in a detector of a medical imaging system and having holes defined by a given cross section, height in inclination and vergence, as well as to a medical imaging system equipped with a collimator of this type. The holes are collected in at least a first and a second region, the holes in the first region being defined by a first cross section, a first height, a first inclination and a first vergence, the holes in the second region being defined by a second cross section, a second height, a second inclination and a second vergence, and wherein the first cross section is different than the second cross section and/or the first height is different than the second height and/or the first inclination is different than the second inclination and/or the first vergence is different than the second vergence. The invention applies, in particular, to gamma cameras.

12 Claims, 3 Drawing Sheets

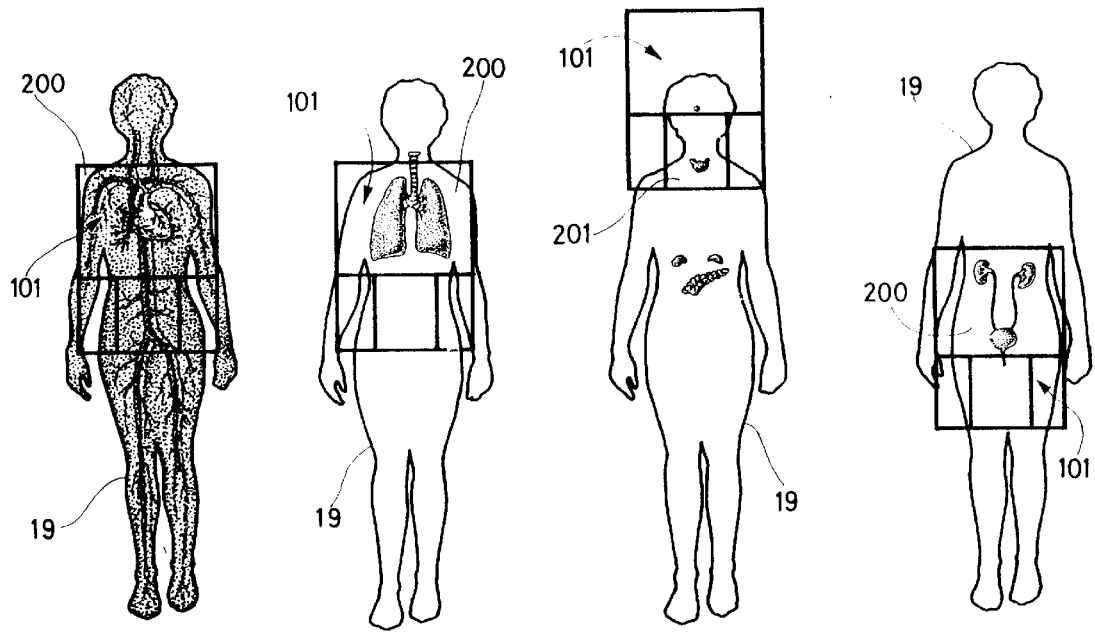
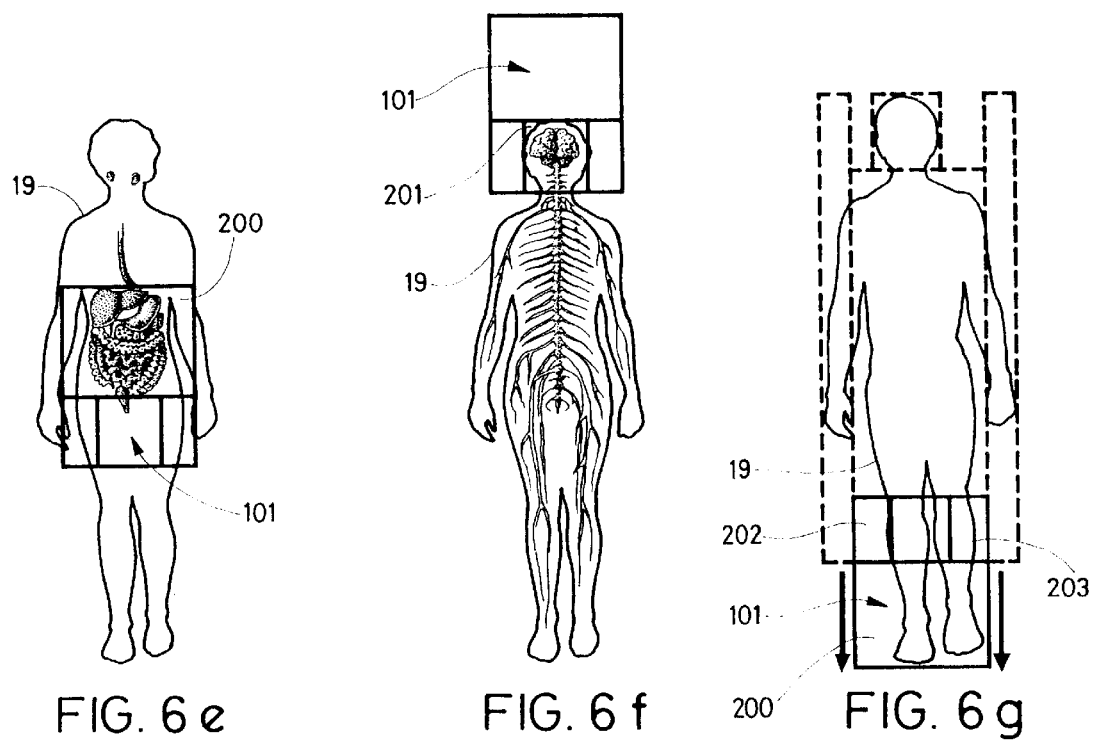
FIG. 6a  FIG. 6b  FIG. 6c  FIG. 6d
FIG. 6e  FIG. 6f  FIG. 6g

COLLIMATOR WITH MULTIPLE FIELD OF VIEW AND A MEDICAL IMAGING SYSTEM INCLUDING A COLLIMATOR OF THIS TYPE

BACKGROUND OF THE INVENTION

The present invention relates to the field of medical imaging. It concerns a collimator intended to be mounted in a detector of a medical imaging system and, in particular, in a gamma camera detector.

Gamma cameras are medical imaging systems provided with at least one detector intended to pick up gamma radiation emitted by a patient, into whose body a gamma-emitting radioisotope marker has been injected. This gamma radiation passes through a collimator and excites a scintillator crystal which converts the energy of said gamma radiation into light energy that is detected by photomultiplier tubes which then produce electrical signals as a function of the luminous intensity received. By performing center-of-gravity location over all these electrical signals, it is possible in known fashion to determine the origin of each scintillation. Taken together, these scintillations make it possible to acquire, for a given angle of view of the detector, a projection revealing the concentration of the gamma-emitting radioisotope marker in the patient's body and, with several projections, obtained for different angles of view, an image of a cross section or a volume of the patient's body is reconstructed.

The collimators are placed in front of and against the detectors, at the entry face of the scintillator. They consist of an absorbent plate pierced by holes whose characteristics, in particular cross section, height, inclination and vergence, are identical. The field of view of the collimator is unique and unitary. Thus, the holes select the gamma rays emitted or transmitted by the patient's body in a given solid angle whose axis is parallel to the direction of the projection which is acquired, whereas the gamma rays that do not correspond to this solid angle are absorbed by partitions delimiting the holes in the collimator.

Certain examinations require the presence of a collimator having very high resolving power, that is to say in which the aforementioned solid angle is narrow, whereas other examinations do not require collimators of this type. For this reason, the collimators of a gamma camera are changed in accordance with the examinations that are performed. Various more or less complex methods have moreover been proposed to this end. One of these methods is described in the French patent published under number FR-2,640,054 and entitled: "système de mise en place d'un collimateur dans une gamma caméra" [system for fitting a collimator in a gamma camera].

In view of the above considerations, the invention proposes to solve the problem of producing a collimator which can be used in different examinations, without needing to be changed.

BRIEF DESCRIPTION OF THE INVENTION

One solution of the invention relates to a collimator intended to be mounted in a detector of a medical imaging system, the collimator having holes defined by a given cross section, height, inclination and vergence, wherein the holes are collected in at least a first and a second region, the holes in the first region being defined by a first cross section, and a first height, a first inclination and a first vergence, the holes in the second region being defined by a second cross section, a second height, a second inclination and a second vergence, and wherein the first cross section is different than the second cross section and/or the first height is different than the second height and/or the first inclination is different than the second inclination and/or the first vergence is different than the second vergence.

Since the holes in each region are different, one region of the collimator is thus better suited than another to a particular type of examination. By selecting the best suited region, and therefore the region which has the appropriate field of view, changing the collimator becomes superfluous.

The following description, which implies no limitation, will clearly show the way in which the invention may be put into practice.

BRIEF DESCRIPTION OF THE DRAWINGS

The description should be read with reference to the appended drawings, in which:

FIGS. 6A, 6B, 6C, 6D, 6E, 6F and 6G schematically present the position of a collimator according to the invention, in the case of different examinations.

DESCRIPTION OF ONE PREFERRED EMBODIMENT

The invention relates to medical imaging devices and, in particular, gamma cameras.

Figure 1:
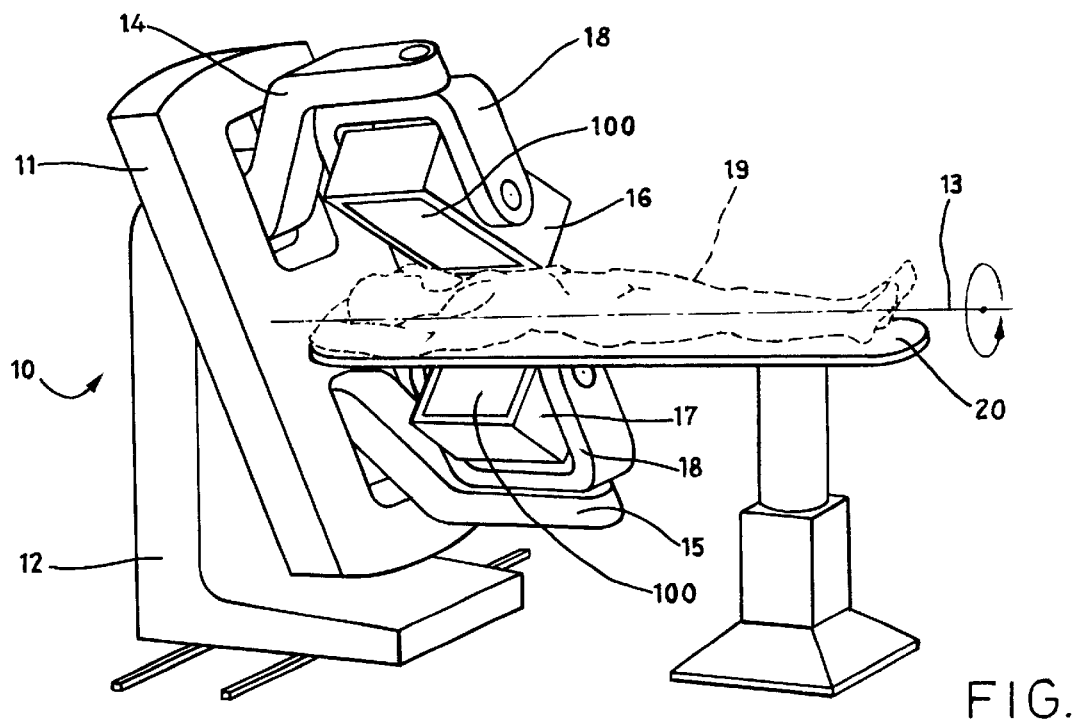
FIG. 1 shows a perspective view of a gamma camera for implementing the invention.

As shown in FIG. 1, a gamma camera 10 for implementing the invention has a base 11 that can move on a frame 12 so as to rotate about an axis 13 referred to as the axis of rotation of the gamma camera. The frame 12 supports two arms 14, 15 the latter arranged symmetrically on either side of the axis 13. At its free end, each arm 14, 15 supports a substantially right-angled parallelepipedal detecting head or detector 16, 17. By way of example, the detectors 16, 17 are attached to the arms 14, 15 by means of a fork joint 18.

Figure 2:
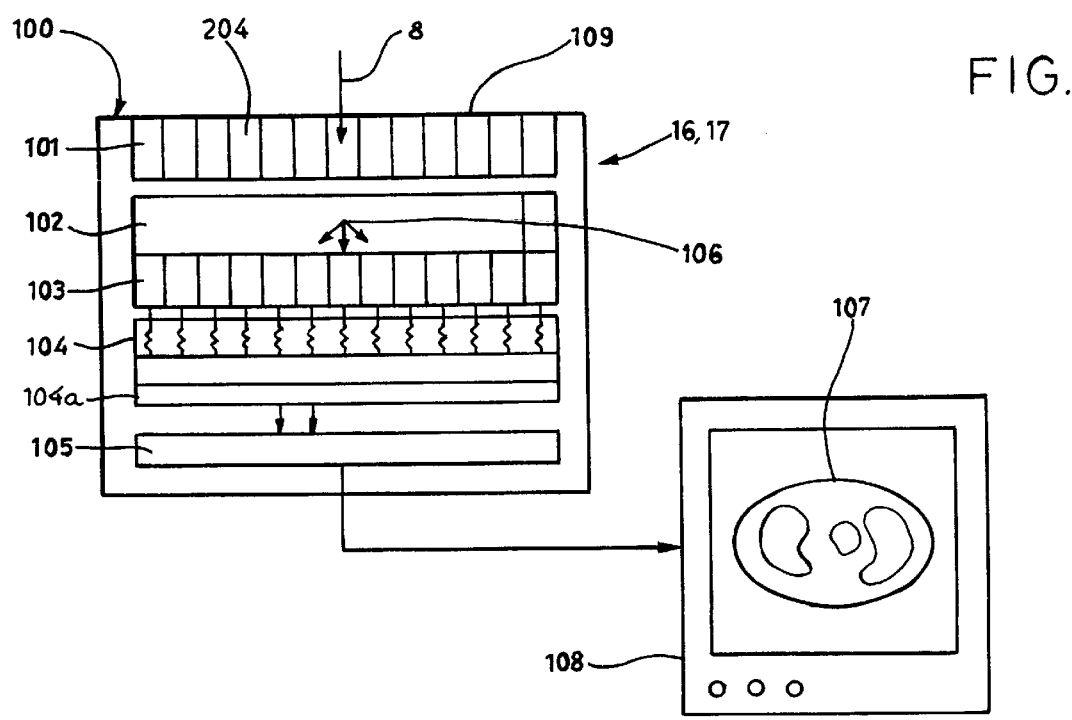
FIG. 2 illustrates, schematically and in section, the operating principle of a detector of a gamma is camera for implementing the invention.

Each detector 16, 17 has an active face 100 that points towards the body 19 of a patient lying on a bed 20, substantially along the axis of rotation 13. In addition, as shown by FIG. 2, starting from its active face 100, each detector 16, 17 comprises a collimator 101, which has a detection surface 109, then a scintillator crystal 102, an array of photomultiplier tubes 103, and signal processing circuits 104 for location, which are connected to an amplification circuit 105.

The principle by which an image of the patient's body 19 is obtained is as follows. For a given position in orientation and angulation of the detectors 16, 17, gamma rays γ emerging from and/or passing through the patient's body 19, which have an appropriate direction of propagation contained within a given solid angle, pass through said collimator 101 and cause a scintillation 106 in the scintillator crystal 102. This scintillation 106 is detected then amplified by the array of photo-multiplier tubes 103, which forms electrical signals for location that are subsequently processed in the processing circuits 104 and are amplified in the amplification circuit 105. This then provides a projection of the patient's body 19 for the aforementioned position and, with several projections, which are obtained for different relative positions of the detectors 16, 17 and of the patient's body 19, it is possible to reconstruct an image of said body 19, for example a sectional image 107 displayed on a monitor 108 connected to the gamma camera 10.

Figure 4:
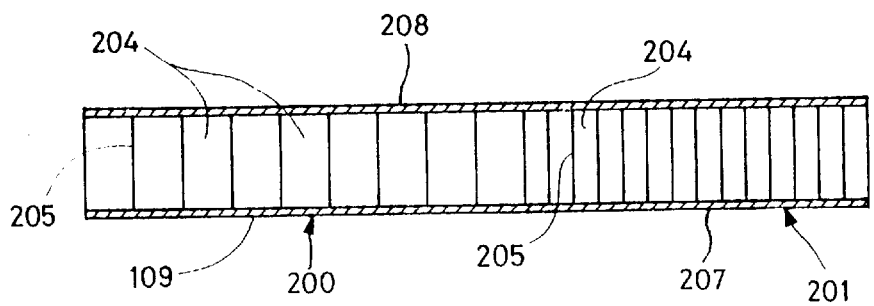
FIG. 4 presents a view, in section on I—I in FIG. 3, of a collimator according to the invention.
Figure 5:
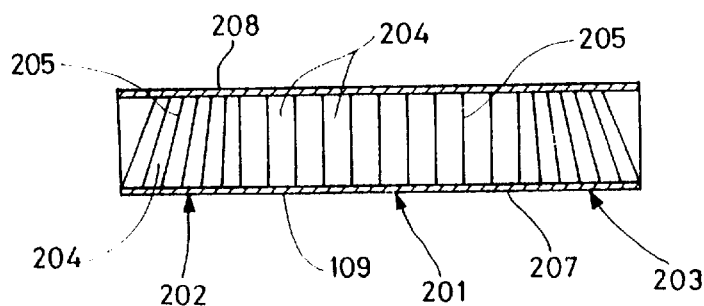
FIG. 5 presents a view, in section on II—II in FIG. 3, of a collimator according to the invention.

A collimator 101 according to the invention consists of an absorbent plate pierced by holes 204 and, in general, covered by protective panels 207, 208 that are transparent to γ radiation (FIGS. 4 and 5). It is divided at least into a first 200 and a second 201 region which each have one or more holes 204 separated by metal partitions 205 of a given thickness, which give said collimator 101 a cellular appearance.

Each hole 204 is defined by characteristics and, in particular, by its cross section s, its depth or height h, its inclination i and its vergence v.

The cross section s of a hole 204 describes a given geometrical profile defined by the partitions 205 and has a surface area.

In one example, the geometrical profile of the holes 204 is hexagonal. Each hole 204 is then defined by a set of six partitions 205 which separate it from six other holes 204. The collimator 101 is then referred to as honeycombed. It is, however, clear that any geometrical profile may a priori suit for the cross section of the holes 204.

As regards the surface area of the cross section s, its value may vary, and may lie between 5 and 30 mm$^2$, for example.

The height h of the holes 204 is defined by the height of the partitions 205. In one example, this height h of the holes 204 is between 30 and 70 mm.

As for the inclination i, it is quite often zero. The holes 204, then orthogonal to the active face 100, are then referred to as right. However, the holes 204 may be oblique, and the inclination i then lies between 0 and, at the limit, 90°.

Finally, the vergence v of the holes 204 may be zero, positive and negative. If the vergence is positive, the holes 204 are convergent and then converge to a focal point or line. If the vergence is negative, the holes 204 are divergent.

The resolution of a collimator 101 depends, in particular, on the aforementioned characteristics of the holes 204 as well as the thickness of the partitions 205 which separate said holes 204. In particular, the resolution is proportional to the height h of the holes 204 and inversely proportional to the surface area of the cross section s of said holes 204.

Figure 3:
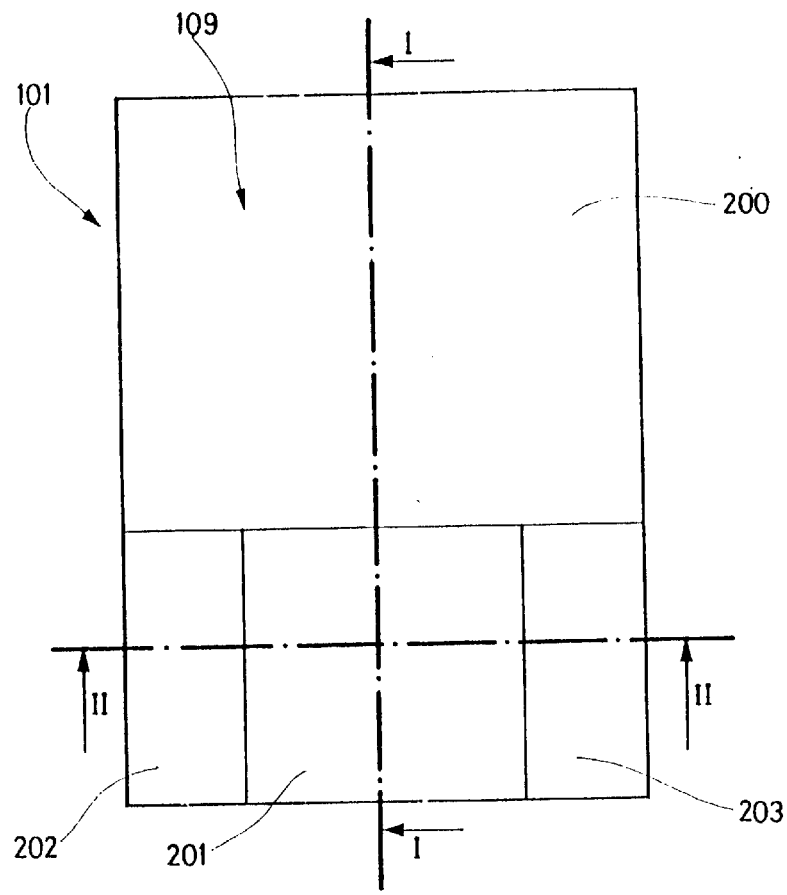
FIG. 3 presents a front view of the detection surface of a collimator according to the invention.

In a particularly advantageous embodiment of the invention, presented in FIGS. 3, 4 and 5, the collimator 101 is composed of a first 200, a second 201, a third 202 and a fourth 203 region.

In each of the four regions 200, 201, 202, 203, the holes 204 are defined by characteristics s, h, i, v. Thus, the holes 204 in the first region 200 are defined by a first cross section, a first height, a first inclination and a first vergence, and the holes 204 in the second region 201 are defined by a second cross section, a second height, a second inclination and a second vergence.

According to the invention, the first cross section differs from the second cross section and/or the first height differs from the second height and/or the first inclination differs from the second inclination and/or the first vergence differs from the second vergence. In other words, the first region 200 has holes 204 which differ from the holes 204 in the second region 200 by at least one characteristic s, h, i, v. Thus, the field of view of the collimator 101 is multiple and the resolving power of the collimator 101 in the first region 200 is normally different from the resolving power of the collimator 101 in the second region 201.

In a particularly advantageous embodiment of the invention, shown essentially in FIG. 3, the detection surface 109 of the collimator 101 according to the invention is substantially rectangular and the regions 200, 201, 202 or 203 are substantially rectangular or square. The first region 200 occupies more than half of the detection surface 109 of the collimator 101, and the second 201, third 202 and fourth 203 regions occupy the complementary part of said surface 109. The dimensions of the third 202 and fourth 203 regions are substantially equal. It can be seen that the first region 200 occupies a greater portion of the surface 109, and the second 201, third 202 and fourth 203 regions occupy a smaller portion of said surface 109. The regions 200, 201, 202 and 203 are distributed symmetrically with respect to a major axis I—I of the collimator 101, that is to say the axis which divides the detection surface 109 into two equal parts and is placed in the length direction of said surface 109. In fact, the first 200 and second 201 regions are distributed symmetrically on either side of the axis I—I, whereas the third 202 and fourth 203 regions are symmetrical to each other with respect to said axis I—I.

In an example in which the detection surface 109 has dimensions of the order of 540×400 mm, the first region 200 has dimensions of the order of 330×400 mm, the second region 201 has dimensions of the order of 210×210 mm and the third 202 and fourth 203 regions have dimensions of the order of 210×90 mm.

The geometrical profile described by the cross section s of the holes 204 in the regions 200, 201, 202, 203 is hexagonal. The surface area of said holes 204 depends on the regions 200, 201, 202, 203. In the first region 200, the surface area of the holes 204 is defined by partitions 205 having a width of 1.9 mm, in the second region 201, said surface area is defined by partitions having a width of 1.5 mm and, in the third 202 and fourth 203 regions, said surface area is defined by partitions having a width of 1.9 mm. The height of the holes 104 is 38 mm for all the regions 200, 201, 202, 203. Moreover, the holes 104 in the first 200 and second 201 regions are right, whereas the holes 104 in the third 202 and fourth 203 regions are oblique, divergent and directed toward the outside of the detection surface 109. Thus, the second region 201 has a greater resolving power than the first 200, third 202 and fourth 203 regions.

It should be noted that the portion of the collimator 101, corresponding to a given region 200, 201, 202, 203, can be changed easily, by hand, and without special tooling. This is true, in particular, of that portion of the collimator 101 which corresponds to the second region 201, which can be changed for a collimator portion with a convergent or stenopaic single hole.

Since the detection surface 109 of the collimator 101 is divided into regions, said collimator 101 has different fields of view. In an examination performed on a patient whose body 19 is placed substantially along the axis I—I, the appropriate field of view is simply selected, and thereby the region or regions 200, 201, 202 or 203 which correspond to that field of view. An electronic mask 104a makes it possible to process only the data originating from the selected field of view.

Thus, for example, for examinations of the heart, lungs, renal system and digestive system, which are presented respectively in FIGS. 6A, 6B, 6D and 6E, these constituting about 56% of the examinations performed with a gamma camera, the field of view corresponding to the first region 200 of the collimator 101 will be selected, given that those examinations do not need a very high image resolution. Conversely, for examinations of the thyroid and the brain, which are presented respectively in FIGS. 6C and 6F, the field of view corresponding to the second region 201 of the collimator 101 will be selected, given that those examinations need a very high image resolution.

For examinations of the whole body, it will be advantageous to select the field of view corresponding to the first region 200 and, possibly, if the detection is to be carried out on the patient's arms, the field of view corresponding to the third 202 and fourth 203 regions. The detectors 15, 16 are then made to scan the body 19 of the patient along the arrows in FIG. 6G. The regions 202 and 203 having divergent holes 204 make it possible to extend the field of view of the collimator 101 to an area greater than the detection surface 109 of said collimator 101.

The subject-matter of the invention is, of course, in no way limited to the embodiment which has been described. In particular, the collimator of the invention may be very well suited to imaging systems, other than gamma cameras, which have one or more detectors.

I claim:

1. A detector for a medical imaging system, said detector comprising:

a collimator, said collimator having holes defined by a given cross section, height, inclination, and vergence, wherein said holes are collected in at least a first region and a second region, the holes in the first region being defined by a first cross section, a first height, a first inclination and a first vergence, the holes in the second region being defined by a second cross section, a second height, a second inclination and a second vergence, wherein the first cross section is different than the second cross section and/or the first height is different than the second height and/or the first inclination is different than the second inclination and/or the first vergence is different than the second vergence, wherein the first region has a resolving power which is different than a resolving power of the second region, and wherein the first region has a field of view which is different than a field of view of the second region; and means for selectively permitting the processing of data originating from only one of the first and second fields of view.

2. The detector as claimed in claim 1, wherein the collimator has a substantially rectangular detection surface, and wherein the first and second regions are substantially rectangular or square.

3. The detector as claimed in claim 1, wherein the first region occupies more than half of a detection surface of the collimator.

4. The detector as claimed in claim 1, wherein the collimator further includes a third region and a fourth region, the dimensions of which are substantially equal to one another.

5. The detector as claimed in claim 4, wherein the third and fourth regions are symmetrical to each other with respect to a major axis of the collimator, and wherein the holes in the third and fourth regions are oblique.

6. The detector as claimed in claim 4, wherein the holes in the third and fourth regions are divergent.

7. The detector as claimed in claim 1, wherein the first and second regions are distributed symmetrically with respect to a major axis of the collimator which divides a detection surface of said collimator into two equal parts.

8. A medical imaging system, which includes a detector as claimed in claim 1.

9. A detector as claimed in claim 1, wherein the means for selectively permitting comprises an electronic mask.

10. A gamma camera comprising:

a frame;

a base which can move on said frame so as to rotate about an axis;

a bed which is configured to support a patient;

first and second arms located above and beneath said bed, respectively; and first and second detectors, each of which is pivotably mounted on a respective one of said arms, wherein each of said detectors includes (1) a collimator which points towards said bed, each of said collimators having holes formed therein, wherein said holes are collected in a plurality of regions, the holes in each of the regions being defined by a cross section, a height, an inclination and a vergence that differ from a cross section, a height, an inclination, and/or a vergence of the holes of at least one other region, wherein at least one of the regions has a resolving power which is lower than a resolving power of at least one other region, and wherein at least one of the regions has a field of view which differs from a field of view of at least one other region, and (2) means for selectively permitting the processing of data originating from less than all of the fields of view.

11. A gamma table as claimed in claim 10, wherein the means for selectively permitting comprises an electronic mask.

12. A method comprising:

providing a collimator having holes formed therein, wherein said holes are collected in a plurality of regions, the holes in each of the regions being defined by a cross section, a height, an inclination and a vergence that differ from a cross section, a height, an inclination, and/or a vergence of the holes of at least one other region, wherein at least one of the regions has a resolving power which is lower than a resolving power of at least one other region, and wherein at least one of the regions has a field of view which differs from a field of view of at least one other region, selecting less than all of the fields of view for processing data originating therefrom, then processing data from only the selected field or fields of view.

* * * * *